United States Patent
Behnisch et al.

(10) Patent No.: US 6,171,450 B1
(45) Date of Patent: Jan. 9, 2001

(54) METHOD FOR PLASMA TREATMENT IN HOLLOW BODIES

(75) Inventors: Jürgen Behnisch, Berlin; Andreas Holländer, Teltow, both of (DE)

(73) Assignee: Fraunhofer-Gesellschaft zur Förderung der angewandten Forschung E.V., München (DE)

( * ) Notice: Under 35 U.S.C. 154(b), the term of this patent shall be extended for 0 days.

(21) Appl. No.: 09/124,005

(22) Filed: Jul. 29, 1998

(30) Foreign Application Priority Data

Apr. 2, 1998 (DE) .............................. 198 14 865

(51) Int. Cl.⁷ ...................................... B01J 19/08
(52) U.S. Cl. .............................................. 204/164
(58) Field of Search ...................... 204/164, 165

(56) References Cited

U.S. PATENT DOCUMENTS

| 5,244,654 | 9/1993 | Narayanan | 424/78.17 |
| 5,486,357 | 1/1996 | Narayanan | 424/78.17 |
| 5,521,351 | 5/1996 | Mahoney | 219/121.59 |
| 5,531,060 | 7/1996 | Fayet et al. | 53/426 |
| 5,677,010 | 10/1997 | Esser et al. | 427/489 |

FOREIGN PATENT DOCUMENTS

| 4408301A1 | 9/1994 | (DE) . |
| 19615735A1 | 10/1997 | (DE) . |
| 19640528A1 | 4/1998 | (DE) . |

*Primary Examiner*—Kishor Mayekar
(74) *Attorney, Agent, or Firm*—Venable; Robert Kinberg; Ashley J. Wells

(57) ABSTRACT

A method for plasma treatment in hollow bodies includes providing a hollow body which has an opening and which is at least partially flexible; evacuating the hollow body with volume contraction to a first pressure which is preselected such that the hollow body, after evacuating and sealing, experiences a volume expansion in the region of a second pressure, by means of which volume expansion the pressure in the hollow body assumes a value which allows ignition of a non-thermal gas discharge in the hollow body; gas-tight sealing the hollow body while maintaining the first pressure; introducing the hollow body, after evacuating and sealing, into a vacuum chamber; evacuating the vacuum chamber to the second pressure; and igniting a gas discharge in the hollow body after sealing by application of an electrical field.

12 Claims, No Drawings

METHOD FOR PLASMA TREATMENT IN HOLLOW BODIES

CROSS-REFERENCE TO RELATED APPLICATION

This application claims the priority of German Patent Application No. 198 14 865.8 filed Apr. 2, 1998, the subject matter of which is incorporated herein by reference.

BACKGROUND OF THE INVENTION

1. Field of the Invention

The present invention relates to a method for plasma treatment in hollow bodies, in particular for plasma-chemical modification of surfaces which are located in the interior of such hollow bodies.

2. Description of the Related Art

Plasma treatment of surfaces plays a major role in many fields of technology. Thus, for example, thin coatings of widely different materials are deposited onto surfaces to be processed, by means of plasma-enhanced chemical vapour deposition (PECVD). The deposited coatings can in this case carry out different functions as an insulation coating, conductivity coating, diffusion barrier etc.

Plasma treatment in the interior of hollow bodies represents a special case group. For example, the plasma treatment of the internal surfaces of medical equipment, such as catheters, can be used to improve their biocompatibility. Such an application is disclosed, for example, in U.S. Pat. No. 5,244,654 or in U.S. Pat. No. 5,486,357.

A further method for plasma treatment is disclosed in U.S. Pat. No. 5,700,327. In the case of this method, an oxidizing process gas is passed into the interior of a container, while a low pressure is maintained in this container. A plasma is ignited in the interior by applying an electrical field to the container, and this plasma has a cleaning effect on the interior of the container.

U.S. Pat. No. 5,677,010 discloses a method in which a polymer coating is deposited in the interior of a fuel tank by means of a plasma-chemical process at reduced pressure. The fuel tank is located in a plasma process chamber, but is connected via a separate gas-tight line to a vacuum pump outside the process chamber. The pressure inside the tank is reduced, via this separate line, further than the pressure in the process chamber. At the same time, a process gas is passed through the tank at a defined speed, via a further line. Owing to the chosen pressure relationships, a plasma is ignited only inside the tank. However, considerable equipment complexity is required to carry out the method since the interior of the tank must be evacuated and supplied with process gas independently of the interior of the vacuumn chamber. This can be achieved only by means of additional gas-tight connections from outside the vacuum chamber to the interior of the hollow body.

A similar method is disclosed in U.S. Pat. No. 5,521,351, the pressure in the interior of the hollow body in this case being selected by metering the inlet and outlet of a process gas in such a manner that the conditions for a gas discharge (plasma) are created in the interior of the hollow body while, by permanent pumping out, the pressure in the process chamber is reduced in such a manner that no gas discharge is possible there. The plasma-chemical modification thus takes place only in the interior of the hollow body. Once again, the equipment complexity is considerable.

One specific application of a plasma-chemical process for sterilization of the internal surfaces of plastic packages is disclosed in U.S. Pat. No. 5,531,060. In this case, the packages are produced by a bubble moulding technique, in which the plastic material is pressed into a prepared mould under the influence of an appropriate gas pressure, this mould corresponding to the shape of the subsequent packaging. The document proposes that a gas which is suitable for the subsequent plasma treatment be used for the bubble moulding and that this gas be enclosed in the packaging by subsequent sealing. The packaging is then placed in a vacuum chamber, is opened at one or more points, and is evacuated together with the vacuum chamber. Finally, when a suitable pressure is reached, a plasma can be ignited in the packaging. In the case of this method, the production process is thus combined at this stage with the subsequent plasma treatment process. There is thus no longer any need to supply process gas in addition to the vacuum chamber. However, the necessity to open the packaging inside the vacuum chamber presents considerable problems.

The object of the present invention is to provide a method for plasma treatment in hollow bodies, which can be used easily and with little equipment complexity, without any modifications to existing plasma systems.

SUMMARY OF THE INVENTION

The invention is achieved by providing a method for plasma treatment in hollow bodies, comprising the following method steps: provision of a hollow body which has an opening and is designed to be at least partially flexible; evacuation of the hollow body with volume contraction to a first pressure which is chosen such that the evacuated and sealed hollow body experiences a volume expansion in the region of a second pressure, by means of which volume expansion the pressure in the hollow body assumes a value which allows the ignition of a non-thermal gas discharge in the hollow body; gas-tight sealing of the hollow body while maintaining the first pressure; introduction of the hollow body into a vacuum chamber; evacuation of the vacuum chamber to the second pressure; and ignition of a gas discharge in the sealed hollow body by application of an electrical field. Additionally provided is a method for plasma treatment in hollow bodies, having the following method steps: provision of a rigid hollow body which has an opening; evacuation of the hollow body to a pressure which allows the ignition of a non-thermal gas discharge in the hollow body; gas-tight sealing of the hollow body while maintaining the pressure; and ignition of a gas discharge in the sealed hollow body by application of an electrical field from the outside to the hollow body. Particular refinements of the invention are the subject matter of the subclaims. Furthermore hollow bodies are disclosed which are designed in accordance with an aspect of the present invention such that their interior can be subjected to a plasma treatment in a simple manner.

DESCRIPTION OF THE PREFERRED EMBODIMENTS

According to the invention, in the case of the proposed method, an at least partially flexible hollow body is used, or a hollow body which is partially composed of flexible material. The hollow body is evacuated by an opening, and is sealed in the evacuated state. Owing to the flexibility of the hollow body, uolume contraction of the hollow body interior occurs during the evacuation. The pressure produced by the evacuation in the interior of the hollow body is chosen such that the volume of the hollow body expands again when the external pressure in a vacuum chamber is reduced, in such a manner that the pressure in the hollow body allows a non-thermal gas discharge when an external electrical field is applied.

Finally, the sealed hollow body is introduced into a vacuum chamber. The vacuum chamber is evacuated to a pressure at which the pressure in the hollow body allows the ignition of a gas discharge in the hollow body.

When the pressure in the vacuum chamber is reduced in such a way, the contracted hollow body "inflates" again. As a result of this volume expansion of the interior of the hollow body, the pressure in the hollow body is reduced until, finally, the conditions for ignition of a gas discharge are achieved. The gas discharge is ignited in a known manner by applying an electrical field to the process volume which contains the hollow body. The gas discharge starts a plasma process, by means of which the internal surfaces of the hollow body are treated.

In this case, sealed packing bags made of polymer films may be used, for example, as hollow bodies, whose surface is intended to be modified, from the inside, possibly including objects packed in them.

It is self-evident that the specified conditions for the evacuation of the hollow body can be maintained only if adequate volume contraction of the hollow body is possible without it being destroyed during the volume expansion.

The person skilled in the art is likewise familiar with the fact that the hollow body must be at least partially composed of dielectric material in order to avoid the interior of the hollow body being shielded from the applied electrical field.

According to a further aspect of the invention, a rigid hollow body can also be used instead of the flexible hollow body. In this case, the plasma in the hollow body can likewise be ignited in a plasma process chamber.

The method according to the invention allows a plasma treatment to be carried out in an advantageous and simple manner in the interior of hollow bodies. In this case, no modification to existing plasma process systems is required. Furthermore, the equipment complexity for carrying out the method is low.

In contrast to the methods known from the prior art, the hollow body in the case of the present method is sealed in a gas-tight manner before the plasma treatment, and remains in this sealed state during and immediately after the treatment.

As a result of the use of the volume contraction of the flexible hollow bodies during the evacuation, it is not necessary to produce a vacuum in the hollow bodies that is hard enough for ignition of a plasma. In fact, a higher pressure is sufficient, which can be produced, for example, by a simple diaphragm pump. The hollow bodies can thus be evacuated and sealed without having to use a technologically complex high-performance vacuum pump, for example even at the production location. Finally, the plasma process can be carried out in any commercial plasma process system without any requirement for additional modifications.

In the case of the method according to the invention, the pressure in the vacuum chamber or process chamber can easily be set to carry out plasma-chemical modification either only in the interior of the hollow body or simultaneously in the interior of the hollow body and in the process chamber. Thus, for example, only the inside of the hollow body or, simultaneously, the inside and outside of the hollow body can be modified. Furthermore in this case, there is no necessity to modify the conventional plasma process chambers.

The nature of the process gas for plasma treatment of the interior of the hollow body can be defined before the plasma treatment by purging with the desired process gas during the evacuation and sealing of the hollow body. The process gas can also be introduced into the hollow body before the evacuation by adding a liquid or solid substance. These substances are changed to the gaseous state by the evacuation.

If the inside and outside of the hollow body are modified simultaneously, different process gases may be used. In this way, for example, the outside of the hollow body can be made hydrophilic (for example in order to achieve a good printing adhesion), while the inside can be provided, for example, with a barrier coating at the same time.

In the case of applications in which only the surfaces in the interior of the hollow body are modified, the use of the method according to the invention advantageously results in no contamination whatsoever in the process chamber, and thus in the entire plasma system, including the pump system.

Furthermore, in this case, the monitoring of the vacuum in the process chamber is not subject to any particular requirements, since, below a specific pressure in the process chamber, the process pressure in the interior of the hollow body is no longer dependent on this pressure. In this case, the pressure in the process chamber need only be less than the pressure at which the volume of the hollow body has completely expanded.

Using the method according to the invention, hollow bodies of different material and shape can be modified simultaneously in one process chamber. Furthermore, by providing different process gases in the various hollow bodies, different plasma processes can be used for modification simultaneously. In the same manner, it is possible to change the process gas in the interior of the hollow body batch-by-batch, without having to carry out any changes to the plasma system.

The method according to the invention offers quite special advantages in those cases in which the aim of the plasma process is to treat an object contained in the flexible hollow body (for example in a film bag). The object is in this case subjected to the plasma treatment in the already sealed hollow body, so that there is no need for any subsequent packaging. In consequence, optimum conditioning is achieved in comparison to a separate plasma treatment with subsequent packaging, during which it is impossible to prevent the object from being contaminated by the environment.

Thus, for example, it is possible to solve those problems which occur in the sterilization of products in the field of biology and medicine. In particular, the plasma treatment in the sealed packaging allows sterilization to be achieved without any further contact with the outside world. Furthermore, the plasma treatment in the sealed packaging can at the same time lead to sterilization and thus to a final product which is packaged such that it is already sterile, for example with the aim of an improved wetting capability or improved biocompatibility of a product. Thus, when the method according to the invention is used, it is possible to dispense with a highly complex, separate sterilization process.

Furthermore, the hollow body in the case of the method according to the invention can also be used as an individual/ separate reaction chamber for any object to be treated, which reaction chamber can easily be disposed of, if required, after the plasma treatment.

The invention will be explained once again in the following text with reference to the fundamental method sequence and with reference to a plurality of exemplary embodiments.

A hollow body which is at least partially flexible, is still open at least one point and is composed of a dielectric material, for example a bag composed of a polymer film, is evacuated according to one of the known methods by pumping it out with partial volume contraction, and is sealed in a vacuum-tight manner. In doing so, an object, for example a polystyrene microtitration plate, may be located in this hollow body. Furthermore, the hollow body can be purged with a specific gas while it is being pumped out, for example with an inert gas such as argon. However, alternatively, a liquid substance, such as HMDSO (hexamethylenedisiloxane), may be introduced into the hollow body before the evacuation. In addition, the hollow body need not be composed entirely of dielectric material. If the process of purging with a specific process gas is dispensed with, then oxygen molecules in the normal environmental air remain in the hollow body after the evacuation, so that the subsequent plasma has an oxidizing effect on the surfaces. Such an oxidizing effect leads to sterilization of the surfaces.

The volume and the geometry of the hollow body, if appropriate taking account of any object enclosed in it, as well as the pressure during sealing of the hollow body are chosen such that an adequately free volume and an adequately low pressure can be maintained in the hollow body throughout the rest of the process sequence. The adequately low pressure of less than 10 mbar as well as the free volume are required in order to make it possible to initiate and maintain an electrical gas discharge in the interior of the hollow body (plasma process).

Depending on the nature of the process gas, the preconditions for ignition of the plasma occur, as a rule, in a pressure range of between 0.1 and 1 mbar. In the case of certain process gases, the pressure levels may, however, also differ from this range.

The hollow body is, finally, placed in the vacuum chamber of a plasma system, for example between the two electrodes in a parallel plate arrangement. A plurality of hollow bodies, which may also differ and be filled with different process gases, can, of course, also be processed at the same time in the plasma system.

The process of pumping out the process chamber then starts. When the pressure is less than the pressure inside the contracted, hollow body, then the volume starts to increase (the hollow body is "inflated"). In this phase of the pumping-out process, the pressure in the process chamber corresponds to the pressure inside the hollow body.

As the pressure in the process chamber is reduced further, the moment is reached at which the hollow body assumes its maximum possible volume. The pressure in the process chamber at this moment corresponds to the lowest pressure which can be achieved inside the hollow body which, after this time, no longer changes even if the pressure in the process chamber is reduced further.

If an electrical field of adequate strength is injected into the process chamber, a plasma is ignited at the point at which the pressure conditions are suitable for plasma ignition. It is possible to distinguish between three possible process regimes, depending on the pressure conditions in the process chamber:

the plasma burns only in the process chamber outside the hollow body;
the plasma burns simultaneously in the process chamber (outside the hollow body) and inside the hollow body; and
the plasma burns only inside the hollow body.

All three process versions can be achieved by appropriately selecting the pressure conditions.

Once the plasma treatment has been completed by switching off the electrical field, the process chamber can be vented and the hollow body removed. The electrical field can, of course, be injected into the process volume by using a multiplicity of electrodes or antenna shapes, as is known to the person skilled in the art in this field. In this case, the injection is preferably carried out using radio frequency or microwave radiation. Suitable plasma systems have been known for a long time.

The method according to the invention is not limited to a specific type of plasma treatment. For example, any desired coatings can be deposited on the internal surfaces. Furthermore, the treatment of the surfaces can be carried out using oxidizing process gases. In principle, any form of modification of surfaces can be carried out by non-thermal plasma using the method according to the invention.

First of all, the three process regimes described above in the process chamber, and their effect, will be illustrated with reference to the following three exemplary embodiments.

First of all, a flat polyethylene bag ($10 \times 10$ cm$^2$), which is not yet sealed at one point, is evacuated by means of a diaphragm pump to a final pressure of about 10 mbar, and is welded closed. This bag is placed between the electrodes of a plasma system, which is fed from an RF generator at 13.56 MHz.

In the case of a first version of the process sequence, the process chamber of the plasma system is pumped out to a pressure of $8 \times 10^{-2}$ mbar. The pressure conditions in the bag are not adequate to ignite a plasma with this external pressure. Thus, by switching on the RF generator (50 watt), a plasma is ignited for one minute in the process chamber only outside the polyethylene bag. As a result of this treatment, the contact angle with water on the outside of the polyethylene bag changes to 52° in comparison with 95° before the treatment, while it remains unchanged at 95° on the inside of the bag. It has been possible to confirm this by measurements.

According to a second process version, the process chamber is this time pumped out to a pressure of $3.5 \times 10^{-2}$ mbar. At this pressure, the conditions for plasma ignition are satisfied both inside the bag and in the process chamber. By switching on the RF generator (50 watts), a plasma is thus ignited simultaneously for one minute in the process chamber outside the polyethylene bag and inside the polyethylene bag, As a result of this treatment, the contact angle with water on the outside of the polyethylene bag was measured to be 52° and on the inside of the bag it was measured to be 48°, in comparison with 95° in both cases before the treatment.

According to the third version, the process chamber is pumped out to a pressure of $1 \times 10^{-2}$ mbar. In consequence, the conditions for plasma ignition are satisfied only inside the bag. By switching on the RF generator (50 watts) in these conditions, a plasma is thus ignited for one minute only inside the polyethylene bag, while no plasma occurs outside the polyethylene bag. As a result of this treatment, the contact angle with water on the outside of the polyethylene bag was measured to be 95°, and that on the inside of the bag was measured to be 49°, in comparison with 95° before the treatment in both cases.

In the case of a further exemplary embodiment, a flat polyethyleneterephthalate (PETP) bag ($10 \times 10$ cm$^2$) which is not yet sealed at one point is evacuated by means of a diaphragm pump to a final pressure of about 10 mbar, is purged with a process gas (hexafluoroethane, C2F6), and is welded closed. This bag is placed between the electrodes of a plasma system which is fed from an RF generator at 13.56 MHz. The process chamber of the plasma system is pumped out and a second process gas (hexamethyldisiloxane, HMDSO) is introduced into the process chamber at a flowrate of 20 sccm. The resultant pressure in the process chamber is 3×10−2 mbar. By switching on the RF generator (50 watts), an HMDSO plasma is ignited for ten minutes in the process chamber outside the polyethylene bag, and a C2F6 plasma is ignited at the same time inside the bag. As a result of this treatment, a siliconorganic plasma polymer coating is deposited on the outside of the polyethyleneterephthalate bag, as it was possible to verify by XPS measurements, while it was possible to measure a water contact angle of 110°, in comparison with 63° before the treatment, on the inside of the polyethyleneterephthalate bag. Furthermore, fluorine was verified in XPS measurements on the inside after the treatment.

In the case of a further exemplary embodiment, a flat sheath (10×15 cm$^2$) which is not yet sealed at one point and is as used for sterile packaging, with a polystyrene (PS) microtitration plate (4×4×1 cm$^3$) located in it, is evacuated by means of a diaphragm pump to a final pressure of 10 mbar, and is sealed. This sealed bag is placed in a plasma system which is fed using a microwave generator at 2.54 GHz. The process chamber of the plasma system is pumped out to a pressure of 1×10−2 mbar. By switching on the microwave generator (250 Watt), a plasma is ignited for 5 minutes within the polyethylene bag in the process chamber, while no plasma is ignited outside. This treatment produces an improvement in the wetting capability, with the microtitration plate being sterilized at the same time. If the closed bag is opened 14 days after the treatment, then the result of this is that even after this time, the microtitration plate can still be wetted completely with water and is biologically sterile.

What is claimed is:

1. A method for plasma treatment in hollow bodies, comprising:

providing a hollow body which has an opening and which is at least partially flexible;

evacuating the hollow body with volume contraction to a first pressure which is preselected such that the hollow body after evacuating and sealing, experiences a volume expansion in the region of a second pressure, by means of which volume expansion the pressure in the hollow body assumes a value which allows ignition of a non-thermal gas discharge in the hollow body;

gas-tight sealing the hollow body while maintaining the first pressure;

introducing the hollow body, after evacuating and sealing into a vacuum chamber;

evacuating the vacuum chamber to the second pressure; and igniting a gas discharge in the hollow body after sealing by application of an electrical field.

2. The method according to claim 1, wherein the second pressure is selected such that a gas discharge is also ignited outside the hollow body in the vacuum chamber when the electrical field is applied.

3. The method according to claim 1, wherein the second pressure is selected such that no gas discharge is ignited outside the hollow body when the electrical field is applied.

4. The method according to claim 1, further comprising purging the hollow body with a first process gas either before or during the evacuation.

5. The method according to claim 1, further comprising introducing, before evacuating, one of a solid or a liquid substance into the hollow body, which one of a solid or a liquid substance forms a first process gas.

6. The method according to claim 4, further comprising introducing a second process gas into the vacuum chamber, which second process gas one of corresponds to the first process gas or has a different composition than that of the first process gas.

7. The method according to claim 1, further comprising introducing, before the hollow body is sealed, an object which is intended to be subjected to a plasma treatment into the hollow body.

8. A method of sterilizing a product, comprising:

performing the method according to claim 7, wherein the object is a product.

9. The method according to claim 7, wherein the hollow body is used as an individual reaction chamber for the object, and wherein the method further comprises disposing of the individual reaction chamber after the plasma treatment.

10. The method according to claim 1, wherein the hollow body is packaging material.

11. The method according to claim 1, wherein sealing is carried out by welding.

12. The method according to claim 1, wherein a plurality of hollow bodies are evacuated and sealed, and are simultaneously introduced into the vacuum chamber so that a gas discharge is ignited in each of the plurality of hollow bodies when the electrical field is applied.

* * * * *